US012673175B2

(12) United States Patent
Slaughter

(10) Patent No.: US 12,673,175 B2
(45) Date of Patent: Jul. 7, 2026

(54) LARYNGEAL ORAL AIRWAY

(71) Applicant: Daniel Slaughter, Austin, TX (US)

(72) Inventor: Daniel Slaughter, Austin, TX (US)

( * ) Notice: Subject to any disclaimer, the term of this patent is extended or adjusted under 35 U.S.C. 154(b) by 171 days.

(21) Appl. No.: 18/388,478

(22) Filed: Nov. 9, 2023

(65) Prior Publication Data

US 2024/0066246 A1 Feb. 29, 2024

Related U.S. Application Data

(63) Continuation-in-part of application No. 16/862,305, filed on Apr. 29, 2020, now abandoned.

(60) Provisional application No. 62/840,155, filed on Apr. 29, 2019.

(51) Int. Cl.
*A61M 16/04* (2006.01)
*A61M 16/06* (2006.01)
*A61M 25/02* (2006.01)

(52) U.S. Cl.
CPC ...... *A61M 16/049* (2014.02); *A61M 16/0431* (2014.02); *A61M 16/0486* (2014.02); *A61M 16/0666* (2013.01); *A61M 2025/022* (2013.01); *A61M 2202/0208* (2013.01); *A61M 2207/00* (2013.01); *A61M 2210/1028* (2013.01); *A61M 2230/432* (2013.01)

(58) Field of Classification Search
CPC .......... A61M 16/0409; A61M 16/0415; A61M 16/0447; A61M 16/0486; A61M 16/0497
See application file for complete search history.

(56) References Cited

U.S. PATENT DOCUMENTS

| 1,498,810 | A | * | 6/1924 | Poe | A61M 16/0493 |
| | | | | | 128/207.14 |
| 5,447,152 | A | * | 9/1995 | Kohsai | A61M 16/04 |
| | | | | | 128/207.14 |
| 6,098,617 | A | * | 8/2000 | Connell | A61M 16/0486 |
| | | | | | 128/207.14 |
| 7,263,998 | B2 | * | 9/2007 | Miller | A61M 16/04 |
| | | | | | 128/207.14 |
| 8,413,658 | B2 | * | 4/2013 | Williams | A61M 16/0488 |
| | | | | | 128/207.14 |
| 8,413,659 | B2 | * | 4/2013 | Crumback | A61M 16/0459 |
| | | | | | 128/207.14 |
| 9,320,864 | B2 | * | 4/2016 | Cook | A61M 16/04 |
| 10,272,228 | B1 | * | 4/2019 | Sharaiha | A61M 16/0459 |
| 2004/0020491 | A1 | * | 2/2004 | Fortuna | A61M 16/0486 |
| | | | | | 128/200.26 |
| 2008/0000481 | A1 | * | 1/2008 | Ganesh | A61M 16/0493 |
| | | | | | 128/207.14 |
| 2008/0308108 | A1 | * | 12/2008 | Diorio | A61M 16/10 |
| | | | | | 128/207.14 |

(Continued)

*Primary Examiner* — LaToya M Louis
(74) *Attorney, Agent, or Firm* — Dorius Law PC; Kirk Dorius

(57) ABSTRACT

A Laryngeal oral airway (LOA) includes a mouthpiece flange defining two separate nostril-like openings in communication with separate elongated airways extending towards the larynx when in use. The nostril-like openings on the mouthpiece are spaced, shaped, and configured to snugly fit nasal prongs a nasal cannula therein, such that the nasal cannula is readily moveable between the patient's nostrils and the artificial nostril openings defined in the mouthpiece of the airway. The cannula is further secured by notches defined in the LOA.

7 Claims, 9 Drawing Sheets

(56) References Cited

U.S. PATENT DOCUMENTS

| 2013/0284181 A1* | 10/2013 | Guerra | A61M 16/0463 |
| | | | 128/207.14 |
| 2015/0367093 A1* | 12/2015 | Clayton | A61M 16/0443 |
| | | | 128/207.15 |

* cited by examiner

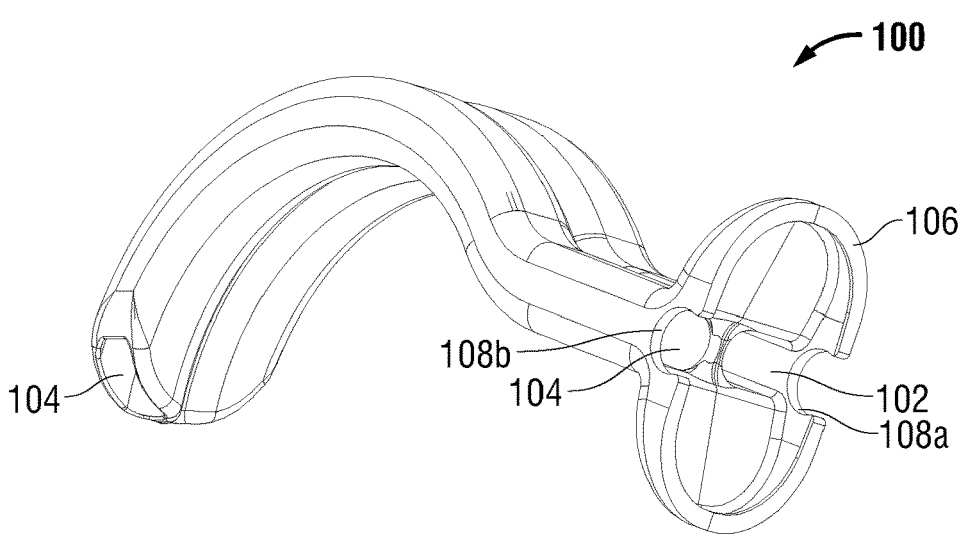
FIG. 6
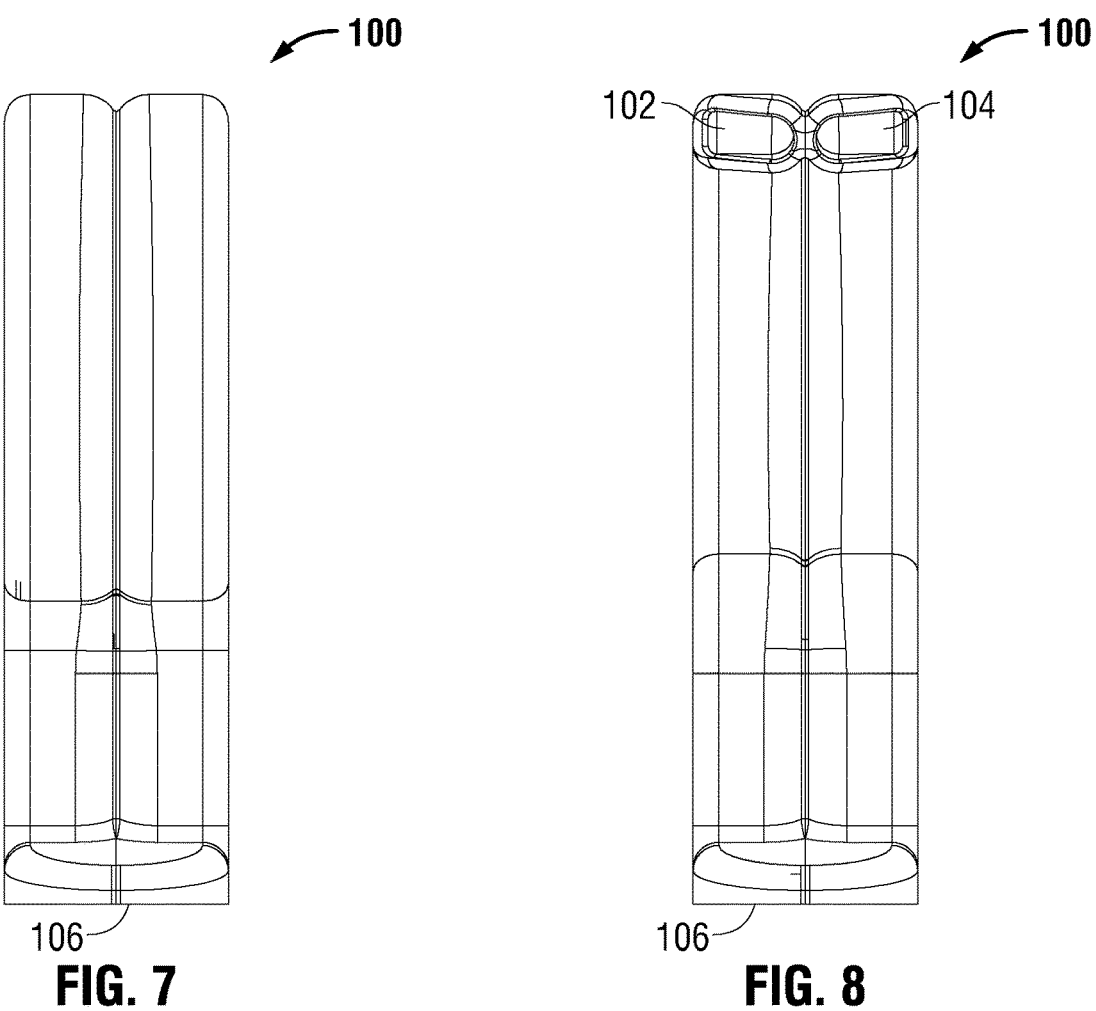
FIG. 7          FIG. 8

1

LARYNGEAL ORAL AIRWAY

CROSS-REFERENCE TO RELATED APPLICATION

This application claims priority to U.S. non-provisional application Ser. No. 16/862,305, filed Apr. 29, 2020, which claims priority to U.S. provisional application Ser. No. 62/840,155, filed Apr. 29, 2019, both of which are incorporated herein in their entireties by reference.

FIELD OF INVENTION

This invention generally relates to oral airways or oropharyngeal airways for use during operations or procedures requiring general anesthesia and also for cases using IV sedation (total intravenous sedation—TIVA).

BACKGROUND OF THE INVENTION

An oropharyngeal airway (also known as an oral airway, OPA, or Guedel-pattern airway) is a medical device used to maintain or open a patient's airway and prevent the tongue from obstructing the airway. During unconsciousness under anesthesia, the muscles in the jaw relax and can allow the tongue to obstruct the airway.

In general, OPA airways include elongated, hard oral airways with a single curved central channel or tube extending from a flanged mouthpiece (See Prior Art FIG. 1A). This type is adequate to keep the airway open during masked ventilation prior to placing an endotracheal tube and immediately after removing an endotracheal tube. One limitation is that the opening is too small to fit a traditional nasal cannula. If the attending physician wants to deliver oxygen in route to the recovery area the nasal cannula can only be placed in the patient's nasal airway. As the patient is mouth breathing with the oral airway in place this is not ideal for oxygen delivery. When sedated patients arrive at the recovery room they may still have the oral airway in for a period of time and with this airway the oxygen delivery continues to be suboptimal and there is no easy way to measure the patient's carbon dioxide. Measurement of a patient's carbon dioxide levels in the recovery room, which is a direct measurement of whether the patient is adequately breathing, is currently considered the standard of care. The nasal cannula is typically placed in the patient's nose with one side delivering oxygen and the other side trying to measure the carbon dioxide levels while the patient is still mainly mouth breathing.

This type of airway also has significant limitations during TIVA sedation cases. These types of cases done in hospitals, surgery centers, and increasingly in surgeon offices do not involve placing a breathing tube. Instead patients are given enough IV sedation to be unaware of the procedure but the goal is for them to remain breathing on their own without a breathing tube or a ventilator. In these TIVA cases an oral airway is commonly placed and kept in throughout the procedure. Using this common design of an oral airway during TIVA is less than ideal as the nasal cannula doesn't fit well into the opening. The patient is mouth breathing and the nasal cannula is sub-optimally delivering oxygen and the measurement of the carbon dioxide at the nostril is with commingled air and delivered oxygen and is suboptimal.

Another popular oropharyngeal airway design includes a curved, elongated web-and-flange I-beam-type structure extending from the flanged mouthpiece (See Prior Art FIG. 1B). This design suffers from similar deficiencies. Although the nasal cannula may be fitted into the opening on each side, the side channels are completed open so there is nothing to direct the oxygen to the laryngeal area as the flange is open to the mouth rather than being a closed channel. In essence, the cannula would just be oxygenating the mouth. The air in the mouth is mixed so the measurement of carbon dioxide is also suboptimal. This common type of oral airway is also not optimal for patient transport to the recovery area or monitoring in recovery room and is also suboptimal for TIVA cases. Thus, both of these prior art designs serve the basic function of keeping the patient's airway open allowing two-way passage of air during respiration. In both such designs, however, inhaled oxygen delivery and monitoring of exhaled carbon-dioxide are suboptimal.

For example, Williams (U.S. Pat. No. 8,413,658) discloses a central scope passage with inlet and outlet tubes/channels in an airway device for simultaneously supplying oxygen and monitoring carbon dioxide. However, the inlet outlet tubes of the Williams device only extend half of the length of the device and do not provide oxygen directly to the larynx at the distal end of the device nor monitoring directly adjacent the larynx at the distal end of the device. Instead, Williams' open distal end of the device mixes the partial inlet and outlet streams in a large open area reducing the effectiveness of oxygen delivery and of capnography/monitoring adjacent the larynx. Williams expressly teaches away from use with a nasal cannula—"With the main airway lumen 12 in place, an ETCO2 monitor line and an oxygen supply line (not shown) are disconnected from the nasal cannula and connected to the ETCO2 line 20 and the O2 line 28 in the respective lateral breathing channels 24 and 32. Once the medical procedure is complete and the patient begins to awaken, the ETCO2 line 20 and the O2 line 28 are disconnected from the ETCO2 monitor and O2 supply, respectively, and reattached to the nasal cannula." (Col 5, Lines 44-55). In other words, Williams teaches discontinuance of use of the nasal cannula rather than enabling continued use of the nasal cannula with the airway device.

Williams could not accommodate a cannula without blocking scope access. The Williams design has a large open central passage/channel and if this is not filled with an endoscope the patient will be breathing in room air through this central passage. The patient will also breathe out carbon dioxide through this central passage. This central passage thus makes for very poor oxygenation and poor capnography when this airway is used for any case besides an endoscopy procedure. Also, Williams large central passage extends well beyond the inlet and outlet tubes, which allows for undesirable mixing of inlet and outlet streams along half the length of the device. This mixing reduces effectiveness of oxygen delivery adjacent the larynx and reduces the effectiveness of monitoring adjacent the larynx. One would not use Williams for cases that do not require a scope, as the patient would be breathing through the large central scope chamber, which would effectively reduce efficiency of both oxygen delivery and capnography. Essentially, Williams and other scope accommodating devices are far too "leaky" and "mixy" to provide controlled oxygen delivery and accurate capnography. Many other prior art designs are similarly "leaky" and "mixy" and do not provide controlled oxygen delivery and accurate capnography.

Practitioners and regulations have come to recognize the value of both accurately delivering oxygen to a patient who is sedated and simultaneously accurately measuring the carbon dioxide exhalation. It is ideally the standard of care that a patient has successful oxygen delivery while being transported to the recovery room from the operating room and also accurate measurement of the carbon dioxide when reaching the recovery room. The measurement of their oxygen saturation is done in the recovery room using the pulse oximeter and the measurement of the carbon dioxide is done by capnography where visible waves corresponding to the patient breathing are seen on a screen. The common single channel or I-beam channel airways have significant limitations as detailed above in the recovery process for sedated patients and during TIVA cases. Some proposed designs incorporate dedicated oxygen cannulas attached along the airway or molded into a sidewall of the central channel with dedicated oxygen-delivery couplings specific to those respective oropharyngeal airway products. However, oropharyngeal airways are considered a disposable item and any such products requiring special-purpose fittings or related equipment changes are unlikely to be adopted.

Accordingly, improvements are sought in delivering oxygen and monitoring carbon dioxide levels during use of oral airways.

SUMMARY OF THE INVENTION

While the way that the present invention addresses the disadvantages of the prior art will be discussed in greater detail below, in general, the present invention provides a novel laryngeal oral airway (LOA) including a mouthpiece flange defining two separate nostril-like openings in communication with separate elongated airways extending towards the larynx when in use. Nostril-like openings on the mouthpiece are spaced, shaped, and otherwise configured to retain a nasal cannula therein, such that the nasal cannula is readily moveable between the patient's nostrils and the artificial nostril openings defined in the mouthpiece of the airway.

Receipt and retention of a conventional nasal cannula into the LOA mouthpiece provides a number of significant advantages, including:

Delivery of oxygen directly to the larynx area through a first artificial nostril opening and respective first airway channel; this design allows the oxygen delivery portion of the nasal cannula to fit down into a closed channel that ends at an opening directed at the larynx/vocal cord area. This provides much improved oxygen delivery during procedures and initial recovery.

Monitoring of carbon dioxide levels of air drawn from a second artificial nostril opening and second airway channel; this allows for a closed channel opening sitting at the vocal cord area to channel the exhalation of air to the nasal cannula port that functions to measure the carbon dioxide exhalation. This provides a much better assessment of patient's breathing at all stages.

Interchangeability of a nasal cannula between the artificial nostril openings of the mouthpiece and the nostrils of the patient is a key advantage. When the sedation wears off and the patient no longer requires the oral airway the nasal cannula can simply be moved to the nostrils where it can then provide oxygen and measure the carbon dioxide.

Operation of the LOA with both mask ventilation and nasal cannulas.

Seamless, continuous monitoring of oxygenation through transition between insertion of the LOA, use of the LOA, and removal of the LOA; the patient starts off having the nasal cannula in their nose in a TIVA case, then the cannula is moved to the new oral airway once it has been placed after the sedation has been given.

Upon awakening the airway is removed and the nasal cannula is placed back in the nostrils.

Reduction in the number of oral airways and insertion procedures required between patient movements from the operating room to recovery areas; the new oral airway can be placed upon sedation in the operating room and used to open the airway for masked ventilation prior to placing the endotracheal tube. It can be re-used after the endotracheal tube has been removed to keep the airway open during transit to the recovery area and allow for easy delivery of oxygen in route, and accurate carbon dioxide measurement when arriving at the recovery area.

In TIVA cases there may be a period where the patient is not breathing voluntarily well enough to maintain adequate oxygen levels. These episodes of hypopnea (reduced breathing) or apnea (cessation of breathing) can cause desaturation of the blood oxygen. The use of this new design provides much better direct oxygen delivery at the vocal cord level, which in turn results in much less tendency for the blood oxygen saturation to drop during these episodes. Its improved oxygen delivery also allows for much quicker recovery of the blood oxygen levels once the patient begins to breathe normally again. The ability also to see more accurately the carbon dioxide exhalation also alerts the physician to these episodes of hypopnea or apnea so they can be addressed earlier and more appropriately. In summary, the novel airway offers reduced likelihood of desaturation, improved recovery of saturation, and faster, more-accurate detection of hypopnea and apnea.

The novel laryngeal oral airway provides a new standard for oral airways to be used in the operating room for mask ventilation that can be used after the surgery in transit to recovery to provide direct and precise oxygen delivery to the patient airway. Once in recovery, the LOA provides direct and precise oxygen delivery as well as accurate CO2 measurement on exhalation when the patient is still sedated. Once the patient is alert, the airway can be removed and the nasal cannula can be moved easily from the artificial nostril openings of the airway mouthpiece to the patient's nose to continue oxygen delivery and carbon dioxide measurement in the awake patient without further airway support.

One aspect of the invention features, in some embodiments, laryngeal oral airway comprising a mouthpiece defining artificial nostril-like openings configured to retain a nasal cannula therein and further comprising discrete airway channels extending from the openings defined in the mouthpiece downward toward a patient's vocal cord area when in use.

In some embodiments, the discrete airway channels are elongated parallel channels. In some embodiments, the elongated channels are substantially coextensive. In some embodiments, the oxygen delivery channel extends further than the CO2 monitoring channel.

In some embodiments, an oxygen delivery channel and CO2 monitoring channel share a common central divider wall. In some embodiments, the oxygen delivery channel and CO2 monitoring channel are formed by injection molding. In some embodiments, the oxygen delivery channel and CO2 monitoring channel are formed by blow molding, and respective first and second portions of the mouthpiece flange are formed with the respective channels and joined during blow molding. In some embodiments, the laryngeal oral airway is formed from multiple components that are snap-fitted, epoxied, or otherwise joined together.

Another aspect of the invention features, in some applications, a method of using a laryngeal oral airway including providing a laryngeal oral airway having a mouthpiece defining a pair of nostril-like openings configured to receive and retain a nasal cannula therein. As with the nasal cannula, a first of the openings conveys oxygen and a second of the openings is used for sampling and monitoring CO2. Oral airways are used to keep the airway open while the patient is unconscious. The mouthpiece can accommodate mask ventilation during surgeries and other procedures. Later, the mouthpiece accommodates a nasal cannula during post-operation recovery. When the patient becomes alert, the nasal cannula is moved from the mouthpiece openings to the patient's nostrils and the airway is removed.

Another aspect of the invention features, in some applications, a method of making a laryngeal oral airway including forming a mouthpiece defining a pair of openings configured to receive a nasal cannula with a first airway channel extending from the mouthpiece for delivery of oxygen near the larynx area, and a second airway channel extending from the mouthpiece for monitoring CO2 during respiration. The second airway channel need be coextensive with the first airway as CO2 levels in respiration can be accurately measured anywhere between the larynx and the lips/nostrils.

The mouthpiece openings can also be used to provide suctioning of the airway during TIVA cases. The opening can accommodate a flexible suction that can be placed at the opening by simply pulling out the carbon dioxide side of the cannula. While continuing to provide oxygen the secretions in the airway can be vacuumed out and then the carbon dioxide cannula is placed back into the opening.

This results in improved patient outcomes through improved oxygenation and CO2 monitoring, e.g., through continuity of ventilation with ready transition from mask ventilation to nasal cannula ventilation through the mouthpiece, to nasal cannula ventilation through the patient's nose. Thus, the novel airway enables the standard of care that oxygen is always delivered effectively and that carbon dioxide is accurately measured during the recovery process. This allows for that to occur as the patient arrives more sedated and having the oral airway in place and then seamlessly moving the cannula to the nostrils as they awaken and the airway is removed. This allows for that same seamless transition during TIVA cases, moving the cannula from nostril to oral airway and back to nostril as the patient goes through the awake to sedated to awake transitions.

BRIEF DESCRIPTION OF THE DRAWINGS

A more complete understanding of the present invention may be derived by referring to the detailed description and claims when considered in connection with the Figures, wherein like reference numerals refer to similar elements throughout the Figures.

FIGS. 2-12 illustrate various views according to one embodiment having a laryngeal oral airway defining discrete air conduits and openings for retaining a nasal cannula therein with minimal mixing with ambient air;

FIG. 2 illustrates a bottom perspective view of the laryngeal oral airway of FIGS. 2-12;

FIG. 3 illustrates a side view of the laryngeal oral airway of FIGS. 2-12;

FIG. 4 illustrates another bottom perspective view of the laryngeal oral airway of FIGS. 2-12;

FIG. 5 illustrates a top perspective view of the laryngeal oral airway of FIGS. 2-12;

FIG. 6 illustrates a perspective view of the laryngeal oral airway of FIGS. 2-12;

FIG. 7 illustrates a top view of the laryngeal oral airway of FIGS. 2-12;

FIG. 8 illustrates a bottom view of the laryngeal oral airway of FIGS. 2-12;

FIG. 9 illustrates a front view of the laryngeal oral airway of FIGS. 2-12, showing the mouthpiece defining openings therein and mouthpiece notches configured to affirmatively retain cannula tubing to retain a conventional nasal cannula within the defined openings;

FIG. 10 illustrates a rear view of the laryngeal oral airway of FIGS. 2-12;

FIGS. 11-12 illustrate side views of the laryngeal oral airway of FIGS. 2-12;

DETAILED DESCRIPTION

Figure 1A:
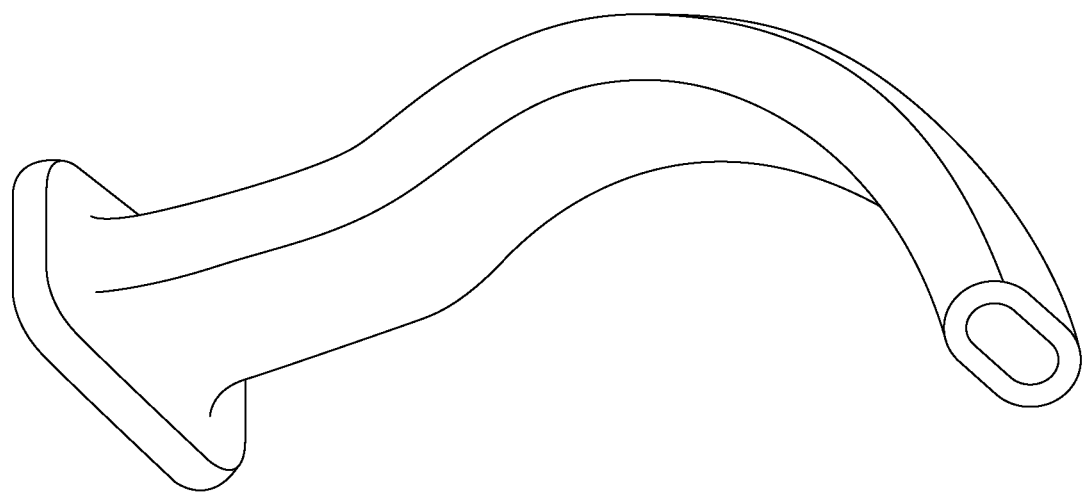
FIGS. 1A-B illustrate Prior Art oropharyngeal devices.
Figure 1B:
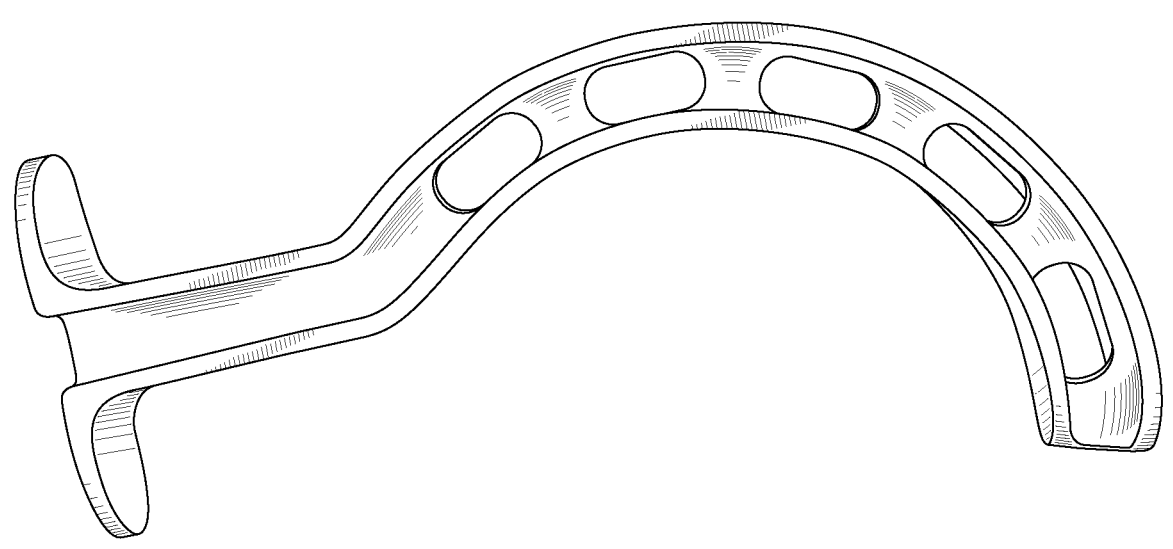
Figure 3:
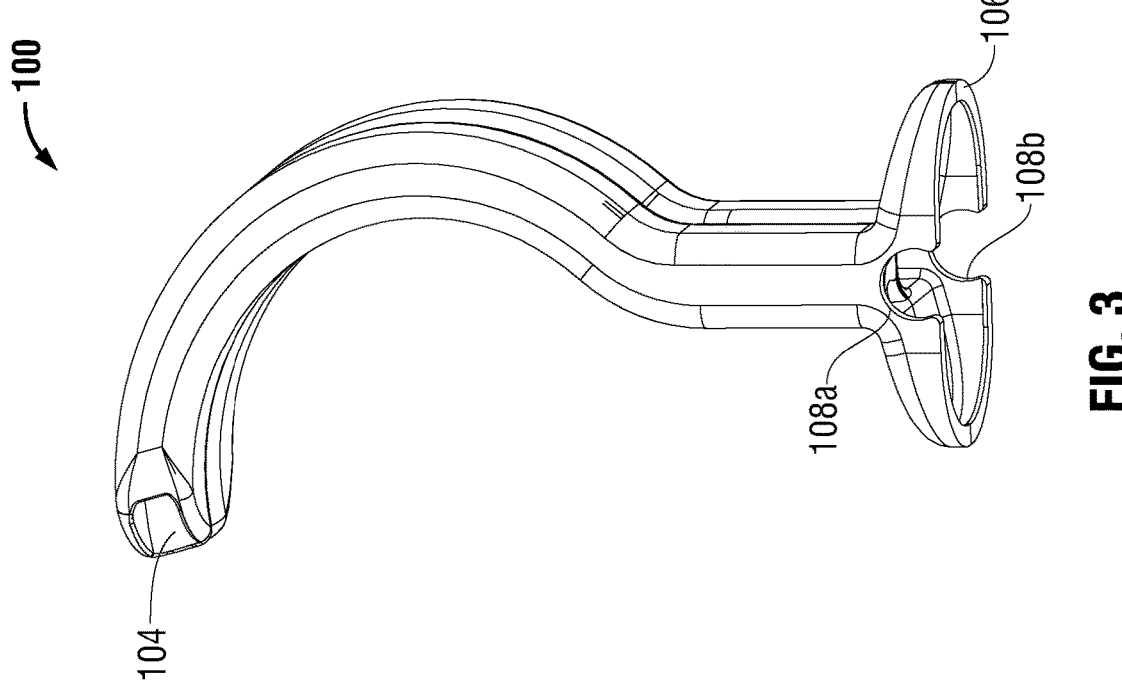
Figure 2:
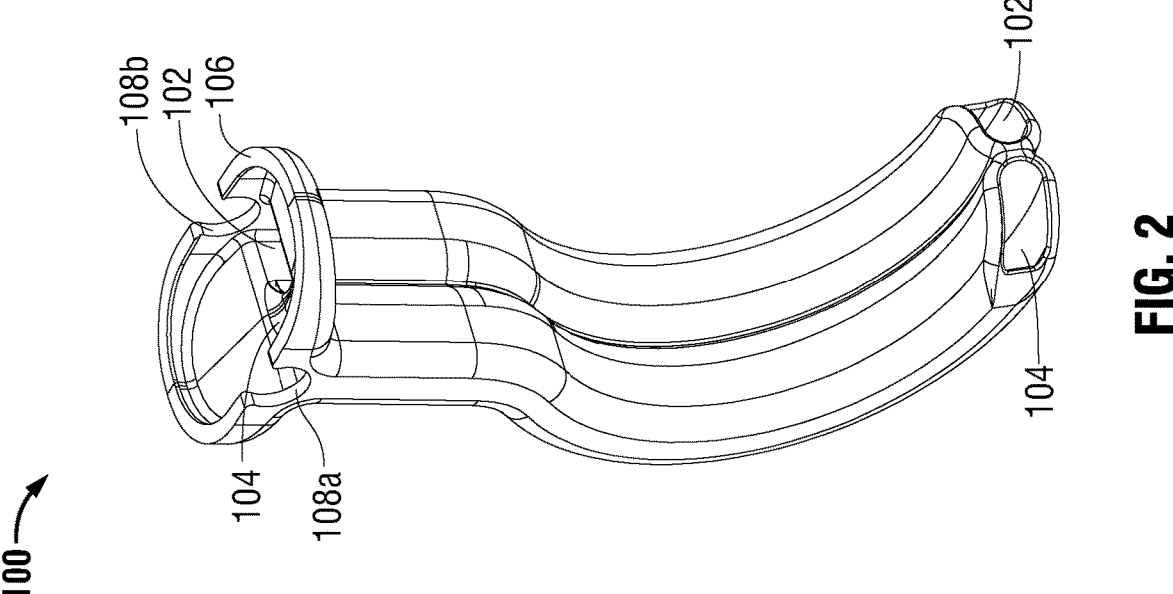
Figure 5:
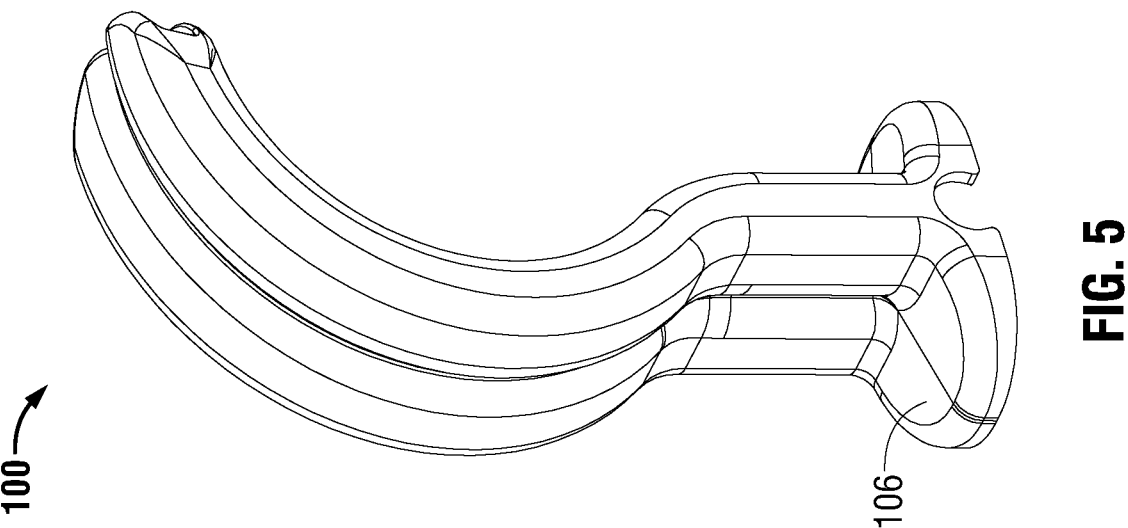
Figure 4:
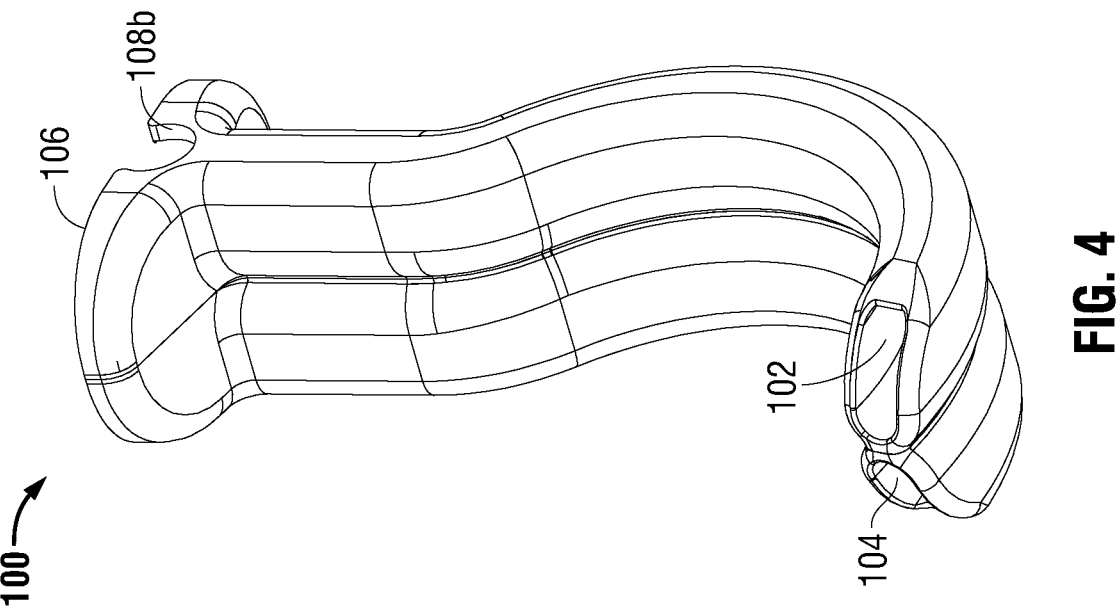
Figure 10:
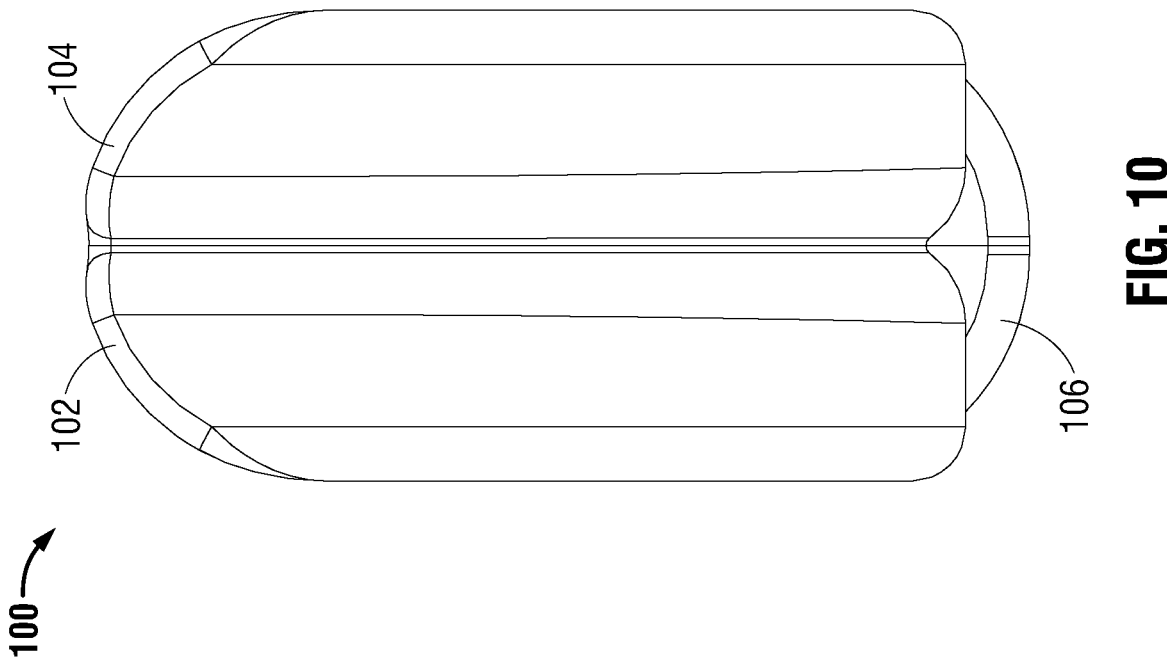
Figure 9:
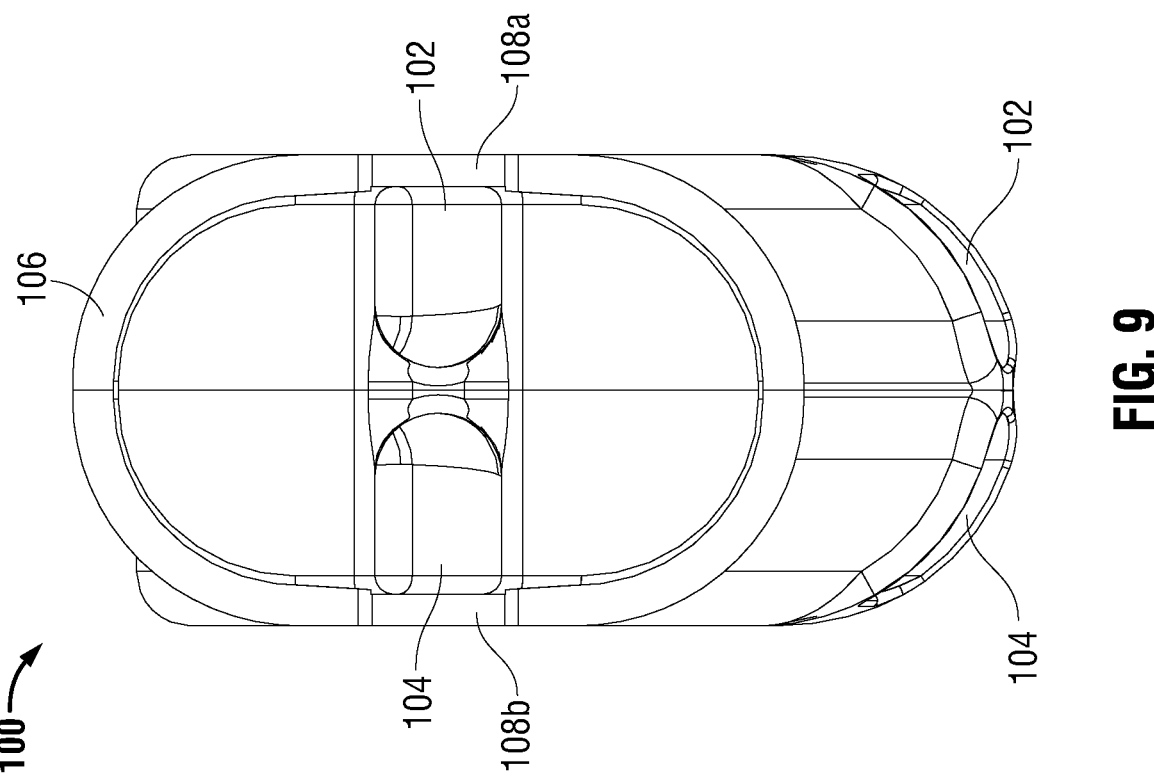
Figure 12:
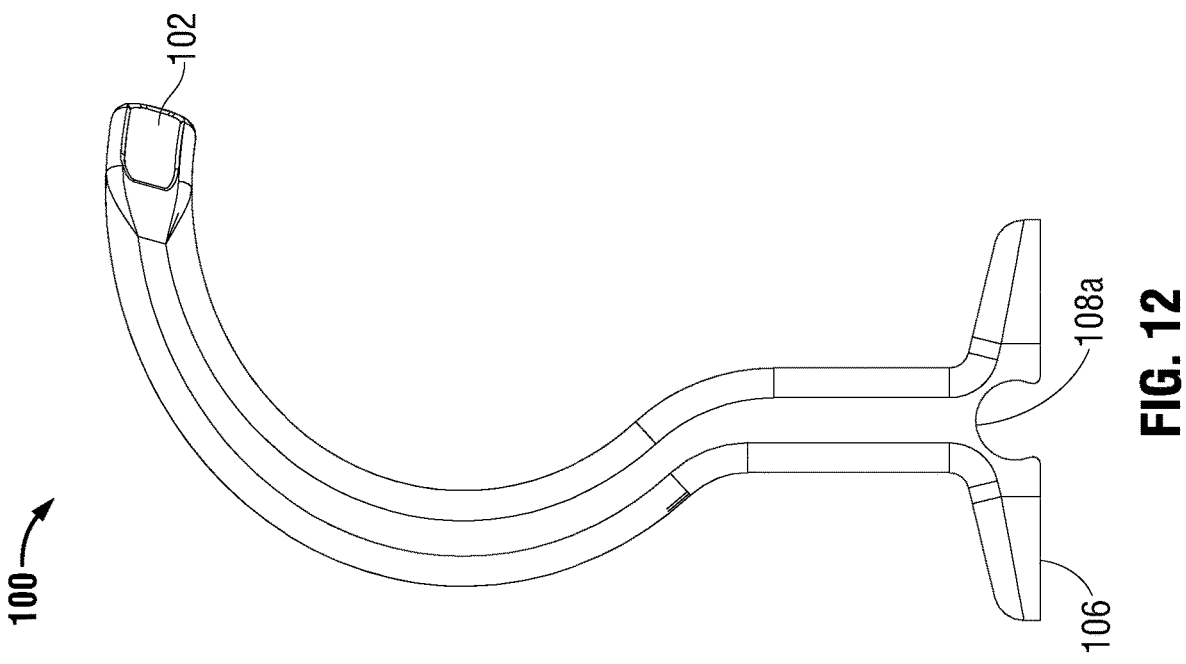
Figure 11:
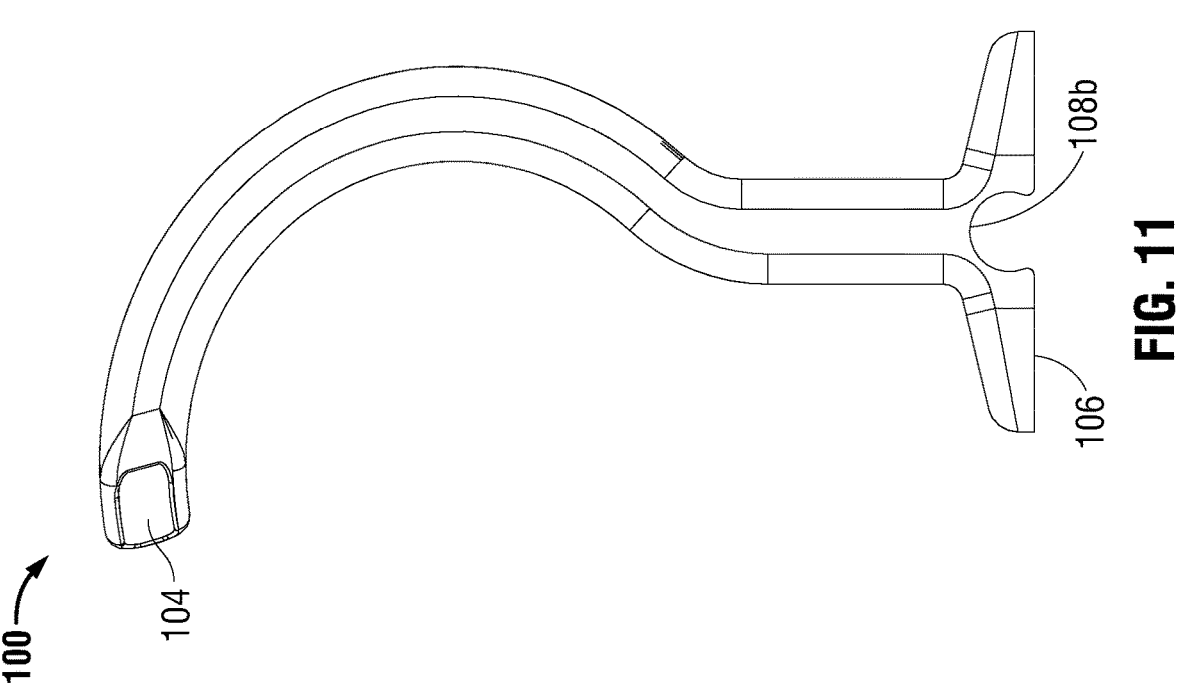
Figure 13:
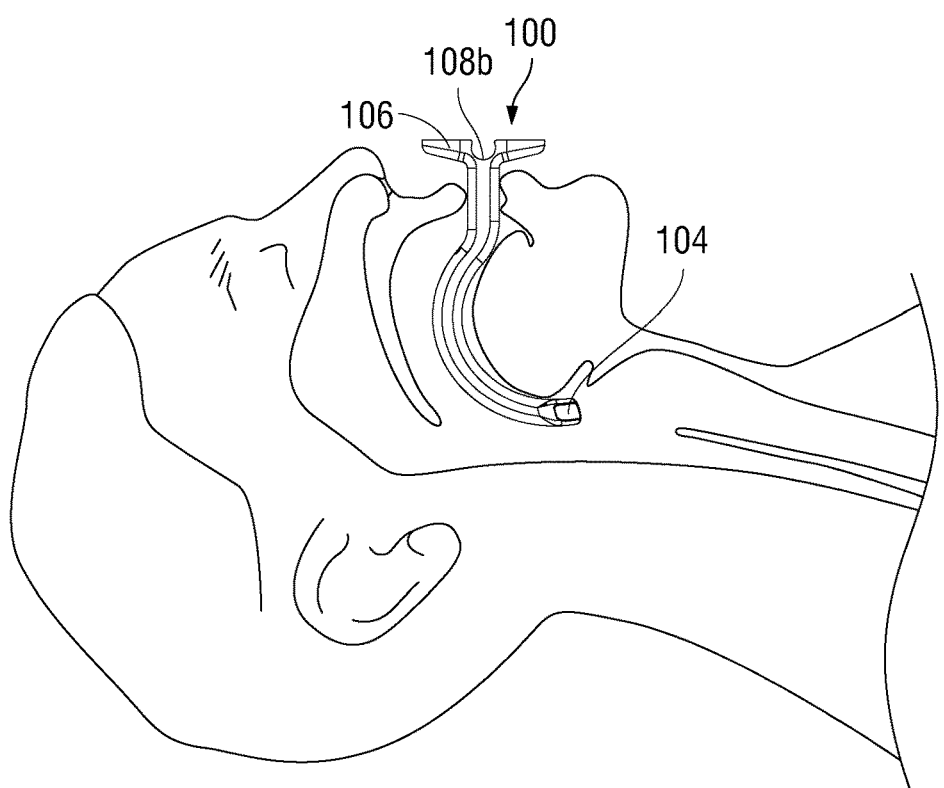
FIG. 13 illustrates a side view of the laryngeal oral airway of FIGS. 2-12, inserted into a patient's airway, e.g., during surgery.
Figure 14A:
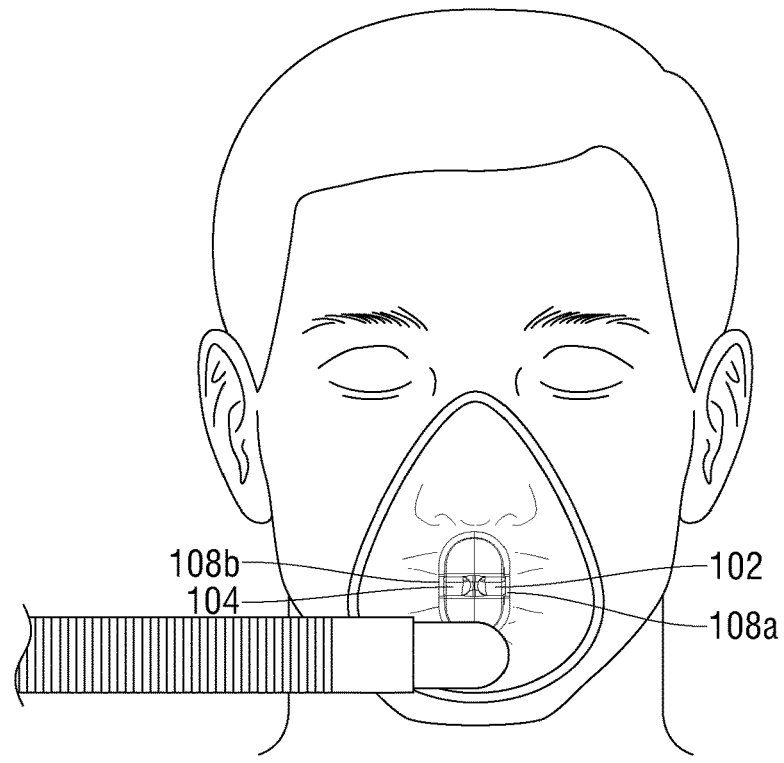
FIG. 14A illustrates a front view of use of the laryngeal oral airway of FIGS. 2-12 inserted into the patient airway providing.
Figure 14B:
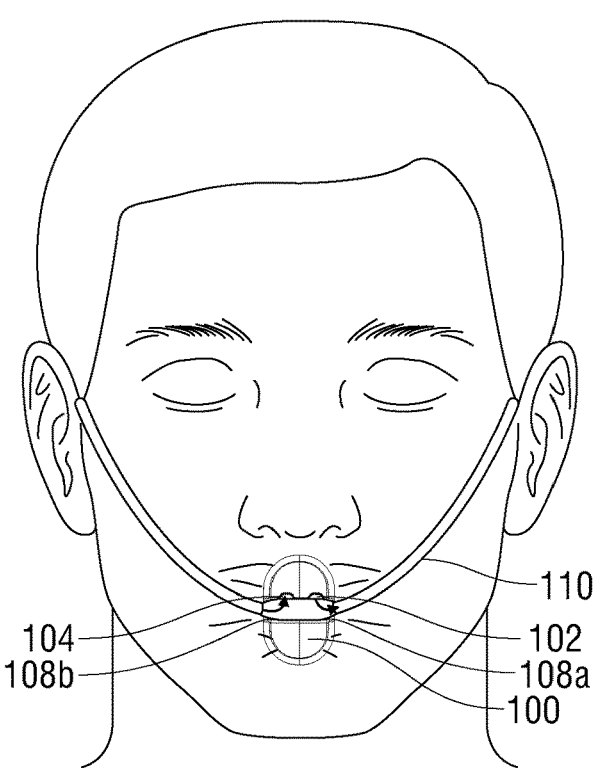
FIG. 14B illustrates a front view of use of the laryngeal oral airway of FIGS. 2-12 inserted into the patient airway and receiving a nasal cannula with sufficiently close fit to prevent ambient mixing and with the cannula tubing retained in the mouthpiece notches.
Figure 14C:
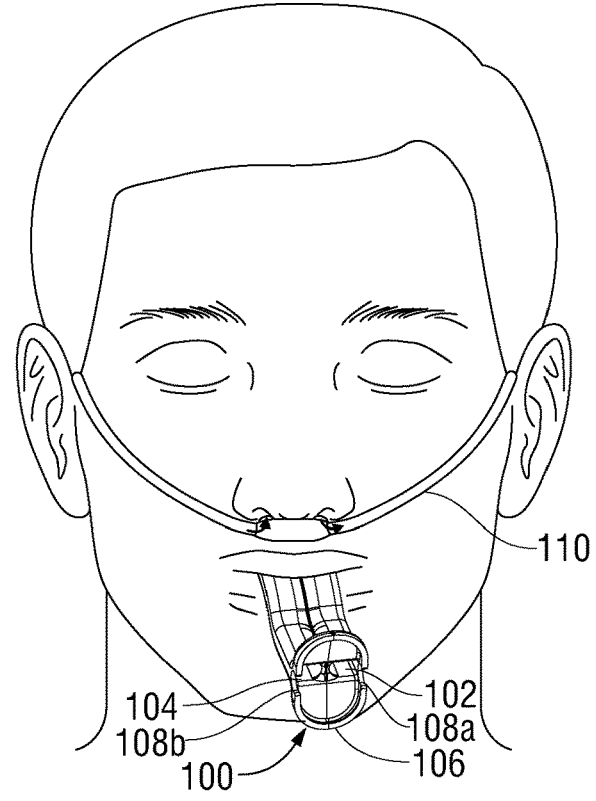
FIG. 14C illustrates a front view of use of the laryngeal oral airway of FIGS. 2-12 being removed from the patient airway after the nasal cannula is moved to the patient's nose.

The following description is of exemplary embodiments of the invention only, and is not intended to limit the scope, applicability or configuration of the invention. Rather, the following description is intended to provide a convenient illustration for implementing various embodiments of the invention. As will become apparent, various changes may be made in the function and arrangement of the elements described in these embodiments without departing from the scope of the invention as set forth herein. It should be appreciated that the description herein may be adapted to be employed with alternatively configured devices having different shapes, components, couplers and the like and still fall within the scope of the present invention. Thus, the detailed description herein is presented for purposes of illustration only and not of limitation.

Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment.

In the following description, certain terminology is used to describe certain features of one or more embodiments of the invention. For example, the term "mouthpiece" as described herein may include, but is not necessarily limited to, a flanged body configured to be retained in a patient's mouth with an exterior flange resting adjacent the lips. For example, the term "channel" as described herein may include, but is not necessarily limited to, a passage, conduit, or other separate conveyance for oxygen and CO2 flows during respiration. The mouthpiece and channels may be constructed from a wide variety of materials including, but not necessarily limited to, plastics, composites, rubbers, etc. It is understood that any process now known or later developed for forming the laryngeal oral airway may be used in accordance with the present invention.

In accordance with various aspects of the present invention, a laryngeal oral airway is provided with discrete oxygen and CO2 channels and respective openings defined in a mouthpiece to receive a nasal cannula therein. The present invention may be used with mask ventilation and with nasal-cannula ventilation. The airway may be removed and the nasal cannula moved to the patient's nose when the patient is sufficiently alert.

FIGS. 2-12 illustrate different views of a laryngeal oral airway (LOA) device 100 according to one embodiment. As can best be seen in FIGS. 2, 6, 9, and 14C, the laryngeal oral airway 100 includes discrete oxygen and CO2 ventilation/monitoring passages 102 and 104 with openings defined in a mouthpiece 106 configured to retain a conventional nasal cannula 108. A conventional nasal cannula 108, i.e., without special-purpose adapters or fittings, is readily movable between the mouthpiece 106 and the patient's nose. The oxygen passage 102 conveys oxygen from a first tube of the nasal cannula 108 into the patient's airway. The CO2 passage 104 releases CO2 for sampling by a second tube of the nasal cannula 108. The nasal prongs of the cannula are snuggly fit in the mouthpiece to substantially prevent ambient mixing. Notches or other features defined on the mouthpiece are configured to retain the tubing attached to the nasal cannula to better secure the cannula to the LOA.

The laryngeal oral airway 100 may be used during operations, general anesthesia, TIVA sedation or other procedures in which the patient's airway may otherwise become blocked. That being said, the present invention is described herein in the exemplary context of a surgery involving general anesthesia and also for TIVA cases. For the purpose of general anesthetic cases, the oral airway would be placed once the anesthesia has been given to support the airway during masked ventilation. It would be removed to allow for the endotracheal tube to be placed. Once the case is over the endotracheal tube is frequently removed when the patient is still sedated and the airway would be placed again to support the airway. It's unique design would allow for more effective oxygen delivery during transit to recovery room, more effective oxygen delivery while still sedated in the recovery area to reduce the risk of low oxygen saturation during episodes of hypopnea or apnea, and it also would allow more effective carbon dioxide monitoring while the patient is still sedated with the airway in place alerting the staff to any problems with respiration. Once the patient is alert and they have regained their normal airway support the oral airway 100 would be removed and the nasal cannula 108 can seamlessly be moved to the nostrils for oxygen delivery and carbon dioxide measurement. This series of advantages also holds true for TIVA cases as the nasal cannula 108 is in the nostrils at the start, moved to the oral airway 100 once sedated, and then placed back in the nostrils once awake allowing for better oxygen delivery and carbon dioxide measurement through the case.

Figure 15:
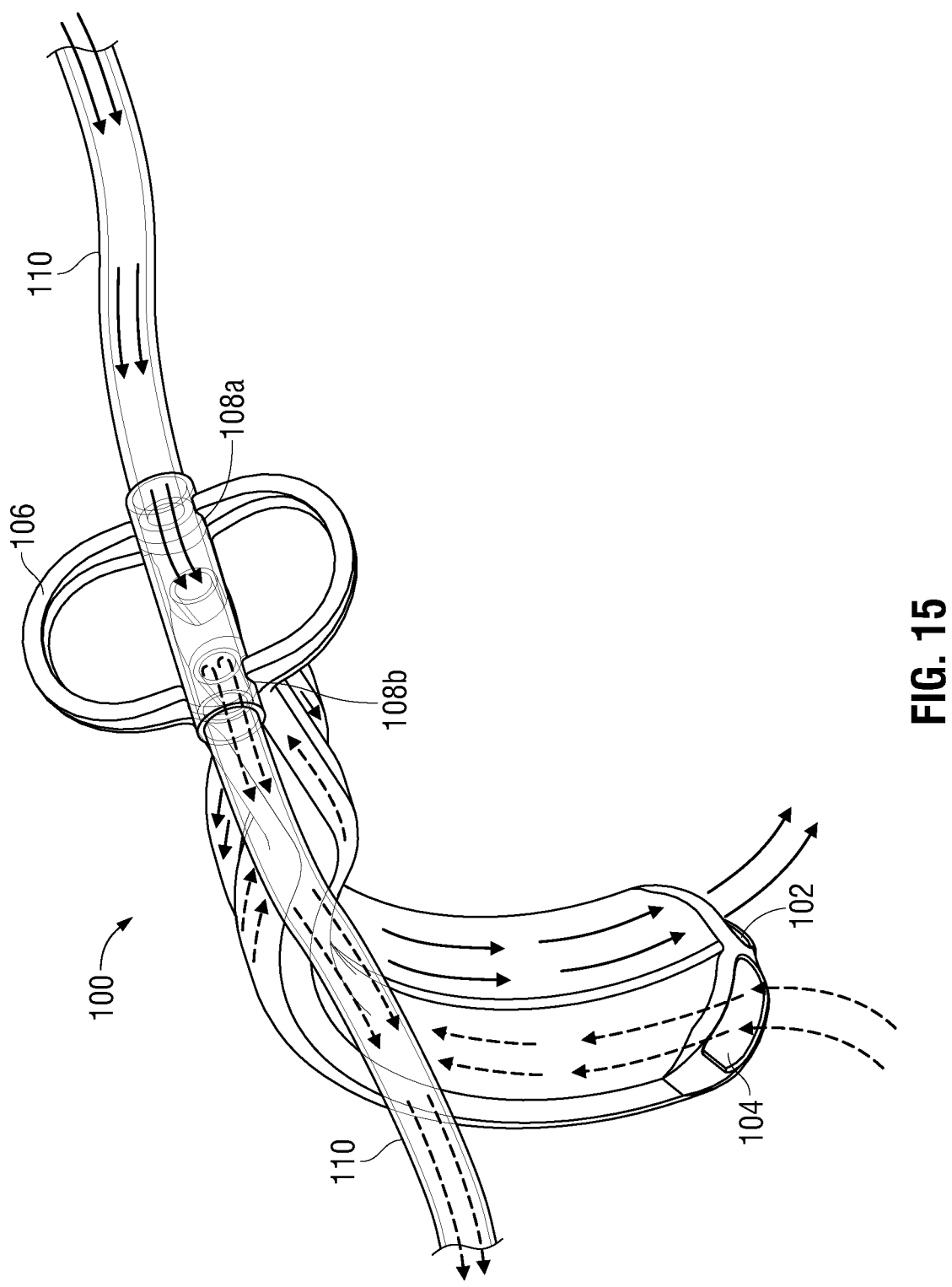
FIG. 15 illustrates directional flow of the oxygen through one side of the cannula and the corresponding first opening/passage and carbon dioxide returning through the other side of the cannula and the corresponding second opening passage in the LOA, with the cannula retained by the notches defined in the mouthpiece.

With reference to FIG. 15, oxygen flows through one side of the cannula and the corresponding first opening and passage 102 for delivery adjacent the larynx, with carbon dioxide returning through the other side of the cannula and the corresponding second opening and passage 104 in the LOA. The cannula is retained in close fitment with LOA 100 by one or more notches 108a and 108b defined in mouthpiece 160. In some embodiments, notches 108a,b retain cannula tubing 110. In some embodiments, notches 108a,b retain a portion of the nasal cannula supporting the nasal prongs. Snug fitment of the nasal prongs within LOA 100 serves to substantially prevent ambient air mixing with the flows inside passages 102, 104. Snug fitment of the nasal prongs, together with snug fitment of tubing 110 in notches 108 a, b serve to retain the cannula safely in place during procedures.

In some embodiments, the airway device provides distinct oxygen supply and monitoring adjacent the larynx, i.e., with each of the first and second elongated airways extending to a distal end of the LOA to respectively deliver oxygen and enable capnography adjacent the larynx when in use; and wherein the first and second openings defined in the mouthpiece flange are spaced, shaped, and configured to retain a nasal cannula therein. Thus, a nasal cannula is readily moveable between the patient's nostrils and the first and second openings defined in the mouthpiece flange of the LOA, with a sufficiently tight fit between the prongs of the nasal cannula and the openings to substantially prevent ambient mixing. In some embodiments, the cannula is further secured in place by notches defined in the mouthpiece and securing the cannula tubing extending to the nasal cannula prongs.

In some embodiments, the airway device has two adjacent but separate passages or channels, a closed oxygen delivery channel and a CO2 measuring channel extending the length of the LOA to simultaneously deliver oxygen adjacent the larynx and monitor adjacent the larynx with minimal channel mixing and minimal ambient mixing. The openings of the passages/channels are spaced and arranged specifically to snuggly fit and retain the nasal prongs of a nasal cannula within the openings of the passage/channel. The fit should provide a sufficiently tight seal so that a high concentration of oxygen delivery arrives just above the vocal cords. The closed channel CO2 measuring channel also rests just above the vocal cords for accurate measurement of carbon dioxide. This is particularly important for IV sedation cases where the patient can be using the nasal cannula and as soon as they fall asleep, the LOA can be inserted and the nasal cannula can easily be transferred to the LOA for continued oxygenation and capnography.

Finally, while the present invention has been described above with reference to various exemplary embodiments, many changes, combinations and modifications may be made to the exemplary embodiments without departing from the scope of the present invention. For example, the various components may be implemented in alternative ways. These alternatives can be suitably selected depending upon the particular application or in consideration of any number of factors associated with the operation of the device. In addition, the techniques described herein may be extended or modified for use with other types of devices. These and other changes or modifications are intended to be included within the scope of the present invention.

The invention claimed is:

1. A laryngeal oral airway (LOA) comprising:
   a mouthpiece flange defining first and second openings spaced generally in proportion to human nostrils;
   first and second distinct elongated airways in communication with the respective first and second openings defined in the mouthpiece flange, each of the first and second elongated airways extending to a distal end of the LOA to respectively deliver oxygen and enable capnography adjacent the larynx when in use;

wherein the first and second openings defined in the mouthpiece flange are spaced, shaped, and configured to receive nasal prongs of a nasal cannula therein; and first and second notches defined in the mouthpiece flange and sized to secure nasal cannula tubing to secure the nasal cannula received in the first and second openings such that the nasal cannula is readily moveable between the patient's nostrils and the first and second openings defined in the mouthpiece flange of the LOA.

2. The LOA of claim 1, wherein the first and second openings are sized to snuggly fit nasal prongs of the nasal cannula to reduce mixing with ambient air.

3. The LOA of claim 1 formed by blow molding.

4. The LOA of claim 3, wherein the first elongated airway is integrally formed with a first portion of the mouthpiece flange and wherein the second elongated airway is integrally formed with a second portion of the mouthpiece flange, and wherein the first and second elongated airways and the first and second portions of the mouthpiece flange are joined during blow molding.

5. The LOA of claim 1 formed by injection molding.

6. The LOA of claim 1, wherein the first elongated airway is configured to deliver oxygen to a patient who is sedated and the second elongated airway is configured to for use in measuring the carbon dioxide during exhalation.

7. The LOA of claim 1, wherein no modification or disconnection of components of the nasal cannula is required to move it between the nostrils of a patient and snug fitment with the first and second openings of the LOA.

\*   \*   \*   \*   \*